US006255097B1

(12) United States Patent
Meyer et al.

(10) Patent No.: US 6,255,097 B1
(45) Date of Patent: Jul. 3, 2001

(54) TWO-PHASE SYSTEM FOR THE PRODUCTION AND PRESENTATION OF FOREIGN ANTIGENS IN HYBRID LIVE VACCINES

(75) Inventors: Thomas Meyer; Johannes Pohlner, both of Tubingen; Frank U. Reuss, Alzenau; Zhengxin Yan, Tubingen, all of (DE)

(73) Assignee: Max-Planck-Gesellschaft Zu Forderung der Wessenchaften, Gottingen (DE)

( * ) Notice: Subject to any disclaimer, the term of this patent is extended or adjusted under 35 U.S.C. 154(b) by 0 days.

(21) Appl. No.: 08/075,491

(22) PCT Filed: Dec. 20, 1991

(86) PCT No.: PCT/EP91/02478

§ 371 Date: Nov. 22, 1993

§ 102(e) Date: Nov. 22, 1993

(87) PCT Pub. No.: WO92/11027

PCT Pub. Date: Jul. 9, 1992

(30) Foreign Application Priority Data

Dec. 20, 1990 (DE) ................................................ 40 41 045

(51) Int. Cl.$^7$ .............................. C12N 7/00; C12N 1/10; A61K 39/00; A61K 35/00
(52) U.S. Cl. .................................... 435/235.1; 435/258.1; 424/278.1; 424/184.1; 424/234.1; 424/200.1; 424/203.1; 424/261.1; 424/93.1; 935/65
(58) Field of Search ............................. 424/278.1, 93.1, 424/184.1, 234.1, 200.1, 203.1, 261.1; 435/258.1, 235.1; 935/65

(56) References Cited

U.S. PATENT DOCUMENTS 4,632,830 * 12/1986 Formal et al. ......................... 424/92
6,040,141 * 3/2000 Klauser et al. .

FOREIGN PATENT DOCUMENTS 0127153   5/1984  (EP) .

OTHER PUBLICATIONS

Tite et al, Immunology. 70: 540–46, 1990.*
Nakasu et al, Virol. , 127: 124–133, 1983.*
Sauer et al, PNAS, 85: 5166–5170, 1988.*
Odell et al, Mol. Gen. Genet. 223: 369–378, 1990.*
Dale et al, Gene, 41: 79–85, 1990.*
Klippel et al, EMBO Journal, 7(12):3983–89, 1988.*
Krasnow et al, Cell, 32: 1313–1324, 1983.*
Reed, Cell, 25:713–719, 1981.*
Klippel et al, EMBO Journal, 7(4): 1229–37, 1988.*
Sadowski, J. Baekeriol. 165(2): 341–347, 1986.*
Murphy et al, Cell, 56: 539–547, 1989.*
Fairweather et al, Infect & Imm. 58(5): 1323–26, 1990.*
Molina et al, Inf. & Imm. 58(8): 2523–28, 1990.*
Maskell et al, Microbial Pathogenesis, 2: 211–21, 1987.*
Poirier et al, J. Exp. Med. 168: 25–32, 1988.*
Sekely et al J. Backnology 155/1:74–81, 1983.*
Zhanget et al Gene 202(1/2): 139–146, 1997.*
Simon et al Science 209(4463): 1370–1374, 1980.*
Black et al. 1987, Prevention of Shigellosis by Salmonella typhi–Shigella sonnei bivalent vaccine, J Infect. Dis., 155(6):1260–1265.*
Clements et al. 1986, Oral immunization of mice with attenuated Salmonella enteritidis containing a recombinant plasmid . . ., Infect. & Immun., 53(6):685–692.*
Clements et al. 1984, Construction of a potential live oral bivalent vaccine for typhoid fever and cholera . . ., Infect. & Immun., 46(2):564–569.*
Tite et al. 1988, Antiviral immunity induced by recombinant nucleoprotein of influenza a virus, J. Immunol., 141(11):3980–3987.*
Formal et al. 1981, Construction of a potential bivalent vaccine strain: Introduction of Shigella sonnei form I Antigen genes . . ., Infect. & Immun., 34(3):746–750.*
Sadoff et al. 1988, Oral Salmonella thphimurium vaccine expressing circumsporozoite protein protects against malaria, Science, 240:336–338.*
Yan et al. 1990, Construction of an invertible DNA segment for improved antigen expression by a hybrid Salmonella vaccine strain, Res. Microbiol., 141:1003–1004.*
Piccini et al. 1986, The use of vaccinia virus for the construction of recombinant vaccines, BioEssays, 5(6):248–252.*
Dougan, 1989, Molecular characterization of bacterial virulence factors and the consequences for vaccine design, J. Gen. Microbiol., 135:1397–1406.*

(List continued on next page.)

Primary Examiner—Nita Minnifield
(74) Attorney, Agent, or Firm—Birch, Stewart, Kolasch & Birch, LLP (57) ABSTRACT

The present invention relates to a genetic engineering process for the optimal production and exposure to the immune system of additional antigen coded for by a live vaccine. The genetic engineering process is based on the use of spontaneous DNA reorganisation in the recombinant live vaccine, such that the recombinant live vaccine spontaneously divides into two subpopulations (A and B), whereby subpopulation A is capable of infecting and acts immunogenically per se as a minimum characteristic and subpopulation B as a minimum characteristic is regenerated by subpopulation A, produces additional antigen and acts immunogenically with respect to said additional antigen. The formation of two subpopulations of the live vaccine ensures, on the one hand, that the infection process necessary for the induction of an immune response takes place and, on the other hand, that the formation of additional antigen by a hybrid live vaccine does not disturb the infection process in order to finally achieve an effective immune response to the additional antigen and the pathogen cross-reacting therewith.

25 Claims, 5 Drawing Sheets-

OTHER PUBLICATIONS

Tijhaar et al. 1994, Construction and evaluation of an expression vector allowing the stable expression of foreign antigens . . ., Vaccine 12(11):1004–1011.*

Klauser et al. 1990, Extracellular transport of cholera toxin B subunit using Neisseria IgA protease . . ., EMBO J., 9(6):1991–1999.*

Lewin, 1985, In: Genes pp. 617–619.*

Borst et al. 1987, Programmed gene rearrangements altering gene expression, Science, 235:658–667.*

Craig, 1985, Site–specific inversion: Enhancers, recombination proteins, and mechanism, Cell, 41:649–650.*

Haynes, 1993, Scientific and social issues of human immunodeficiency virus vaccine development, Sceince, 260:1279–1286.*

Dougan et al., 1989, Live bacterial vaccines and their application as carriers for foreign antigens, Adv. Vet. Sci. Comp. Med., 33:271–300.*

Fox, 1994, No winners against AIDS, Bio/Technology 12:128.*

N. D. F. Grindley et al., Ann. Rev. Biochem., vol. 54, pp. 863–896 (1985).

I.E. Corthesy–Theulaz et al., *Detection and Immunity*, vol. 66, No. 2, pp. 581–586 (1998).

* cited by examiner

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 62 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

```
GGATAAACCG ATACAATTAA AGGCTCCTTT TGGAGCCTTT TTTTTTGGAG ATTTTCAACG     60

TG                                                                    62
```

(2) INFORMATION FOR SEQ ID NO:2:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

```
GATCATTTAC CGTTTCCTGT AAACCGAGGT TTTGGATAAC                           40
```

(2) INFORMATION FOR SEQ ID NO:3:

(i) SEQUENCE CHARACTERISTICS:
(A) LENGTH: 206 base pairs
(B) TYPE: nucleic acid
(C) STRANDEDNESS: single -continued

```
        (D) TOPOLOGY: linear (ii) MOLECULE TYPE: DNA (genomic)

(xi) SEQUENCE DESCRIPTION: SEQ ID NO:3:

TCGAGGTAGC GAGCTTGAGG CATCAAATAA AACGAAAGGC TCAGTCGAAA GACTGGGCCT      60

TTCGTTTTAT CTGTTGTTTG TCGGTGAACG CTCTCCTGAG TAGGACAAAT CCGCCGGGAG     120

CGGATTTGAA CGTTGCGAAG CAACGGCCCG GAGGGTGGCG GGCAGGACGC CCGCCTTAAA    180

CTGCCACAAG CTCGGTACCG TTAACG                                         206
```

TWO-PHASE SYSTEM FOR THE PRODUCTION AND PRESENTATION OF FOREIGN ANTIGENS IN HYBRID LIVE VACCINES

BACKGROUND OF THE INVENTION

The method common in medicine of producing effective protection against infectious diseases in human beings and animals is based on the principle of active immunisation by using pathogen-specific antigens. There are, for example, prophylactic vaccinations against a number of diseases in human beings which are caused by bacteria or viruses. However, vaccinations against fungi and parasites are possible in principle too.

The basis for the protective effect of such vaccines is that important antigens, which in general originate or are derived from the pathogen, are brought into contact with the immune system of human beings or animals by infection or another suitable administration so that a specific immune response directed to the administered antigens is induced. The aim and object of this is to select the administered antigens in such a way and to present them to the immune system such that the induced immune response is directed against the pathogen and a subsequent infection is thus prevented. The induced immune response can be of either humoral (based on antibodies) or cellular nature or both.

The vaccine containing or forming antigens can be constructed or composed in a different way (see Bloom, Nature, 342:115–120, 1989). A simple method consists in using killed pathogens as the vaccine. Improvements are often achieved by only employing a few isolated components of the pathogen in the vaccine which represent important antigens. Moreover, new vaccines often only contain a few well-defined (e.g. purified from the pathogen, or prepared by genetic engineering or otherwise) components which act as an antigen by suitable presentation. Furthermore, every combination of the cited possibilities is conceivable. The common factor of the vaccines is that they consist of inactivated antigen material.

In contrast to these inactivated vaccines, the further possibility of immunising with biologically intact pathogens (so-called live vaccines) and conveying effective protection has long been known. Vaccination with living viruses (Zanetti, Immunology Today, 8:18–25, 1987) and BCG bacteria (Lotte, Adv. Tuberc. Res. 32:107–193, 1984) fall under this category, for example, as well as oral immunisation with living Ty21a Salmonella (Germanier, J. Infect. Dis. 131:553–558, 1975). The principle of such live vaccines is based on the use of an attenuated (or immunologically related non-virulent for a certain species) pathogen strain which is able to cause infection and effective immunological protection against the actual pathogen but is no longer pathogenic per se. Experience in the application of live vaccines lies above all with viruses and bacteria; in principle, however, similar vaccines can also be developed on the basis of fungi and parasites. Live vaccines often have advantages over comparable inactivated vaccines because they e.g. convey better immunological protection and are safer and less expensive.

New developments have furthermore shown that it is possible to change live vaccines by genetic engineering so that they not only present their own antigens to the immune system but also additional antigens which are derived from a different pathogen species. With such hybrid live vaccines it is possible to achieve immunological protection not only against the pathogen from which the live vaccine is derived or with which it is related but also against pathogens against which the immune response to the additional antigen is directed. Depending on the species on which the live vaccine is based, one or more additional antigens can be presented to the immune system and immunological protection can thus be conveyed. This is already realizable in practice with viral and bacterial live vaccines (see Dougan, J. Gen. Microbiol. 135:1397–1406, 1989). In contrast to bacterial or other cellular live vaccines, it is however natural for viral live vaccines (as well as for viruses in general) to be able to express their genetic information only after infection of a cell. In this case the formation of additional antigen by a viral live vaccine consequently requires the infection of cells of the individual to be protected. The presentation of additional antigens to the immune system can on the one hand take place via the infected cell per se or on the other hand via the viral live vaccine which carries additional antigen in its packaging.

A considerable problem with the construction and use of such hybrid live vaccines is however the circumstance that the production of additional antigens often changes the biological properties of the live vaccine and destabilizes the immunological effect so that the desired immunological protection is not achieved or only to a reduced extent. This can be the case in particular if the additional antigen is produced in large quantities as would often be required for the induction of a good immune response, and/or if the additional antigen is otherwise toxic for the live vaccine itself. In other words: The hybrid live vaccine behaves differently to the original live vaccine with respect to the course of an infection and thus with respect to its immunisation potential because it produces one or more additional antigens. This also means that, depending on the kind of additional antigens produced by the live vaccine, the infectious properties and the effectiveness of the immunisation of the live vaccine cannot be inferred in so far as it is at all possible to achieve an effective immune response.

Figure 1:
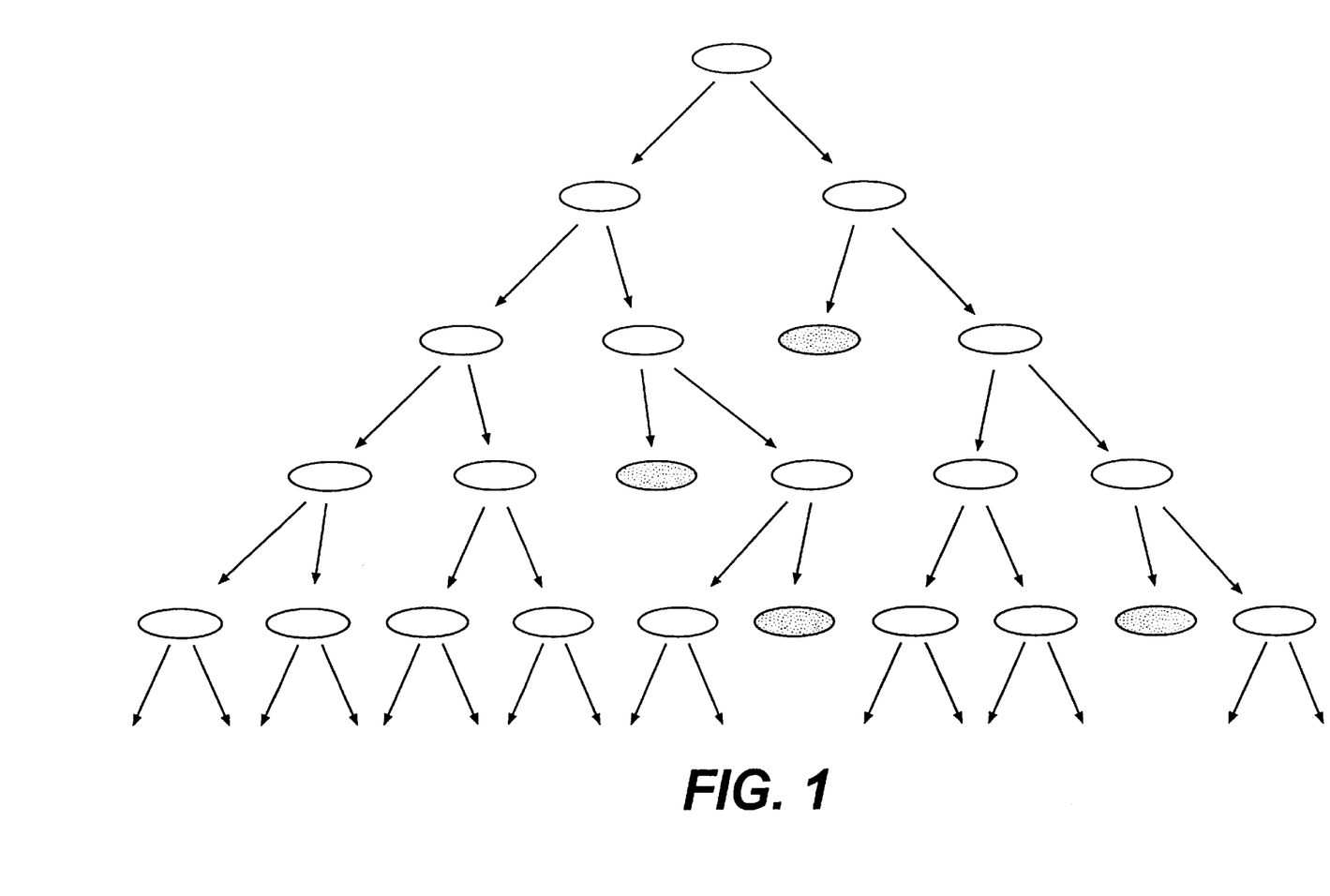
FIG. 1 is an idealization of the exponential reproduction of one cell of the live vaccine (e.g. of a bacterium) which carries a genetic element according to the present invention which leads to the spontaneous formation of two subpopulations/phases A (open ellipses) and B (closed ellipses). While cells remain reproductive in phase A and therefore capable of infecting, spontaneously formed cells of phase B form large quantities of additional antigen which, on the one hand, leads to the induction of an additional immune response but, on the other hand, may inhibit the further reproduction of phase B. In the presented case the frequency of the formation of phase B is about 20%.
Figure 2A:
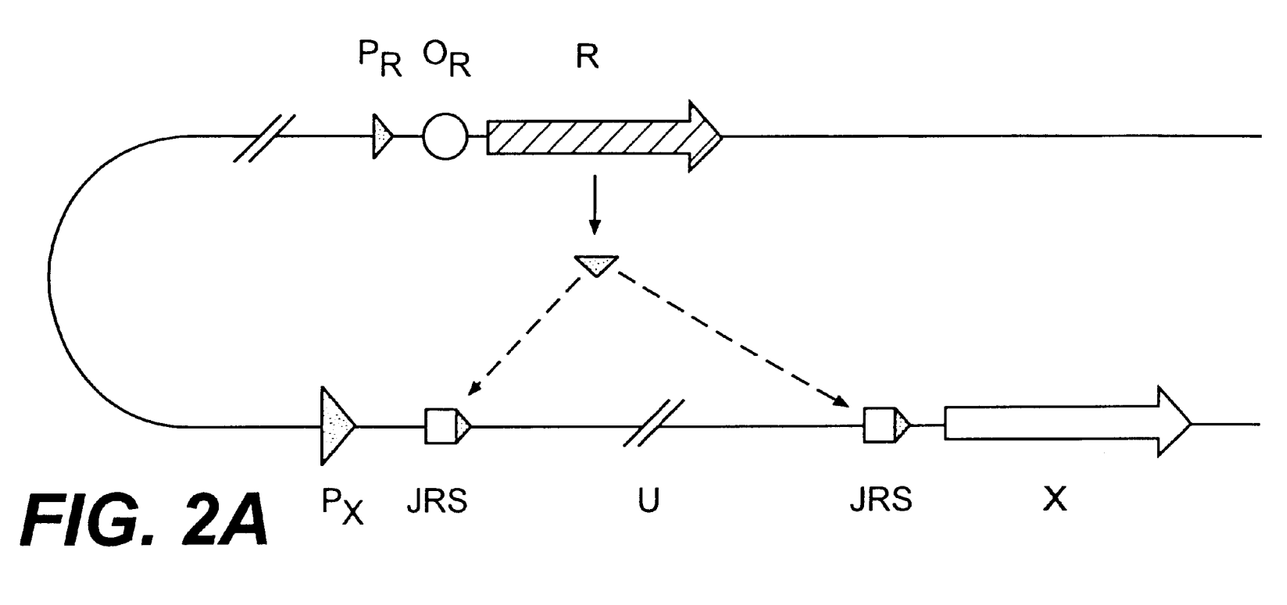
Figure 2B:
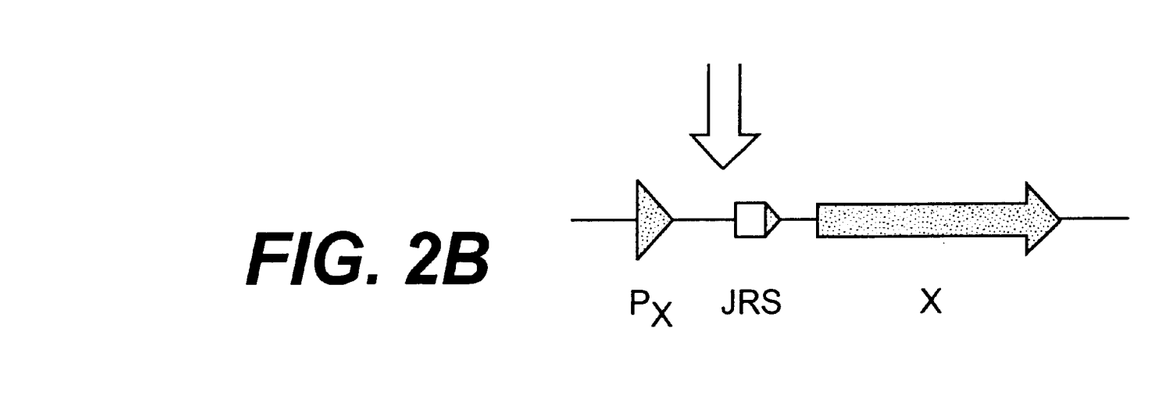
Figure 3A:
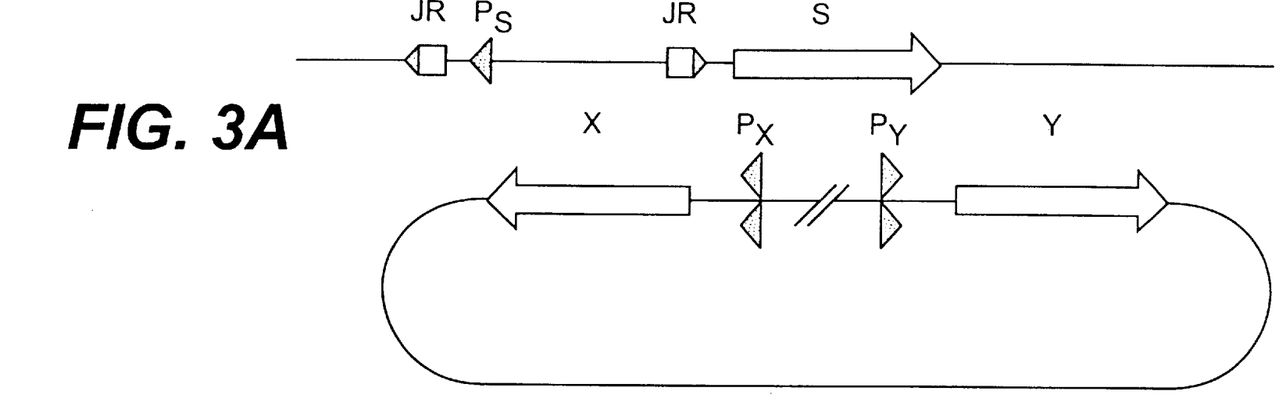
Figure 3B:
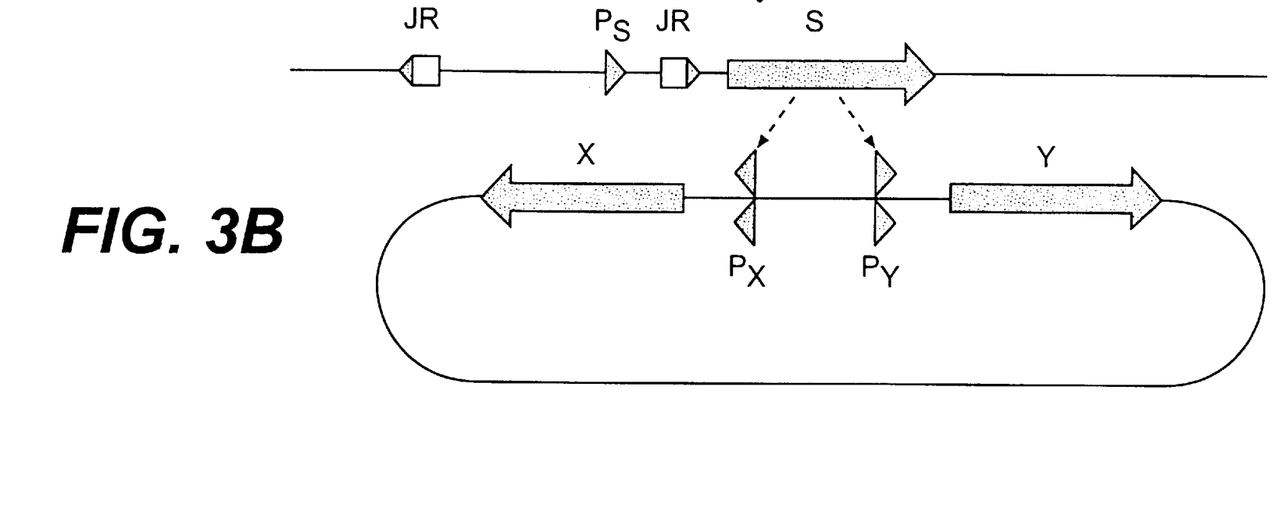

Current experiments to solve this problem in bacterial systems pursue the goal of controlling the formation of additional antigens in a live vaccine by external influences, i.e. to bring the genes which code for the formation of additional antigens under the control of an inducible promoter. The additional antigens of the live vaccine would consequently only be formed in dependence on their external influences or the environment. Such external influences can be e.g. a certain substance or a certain temperature (e.g. lac system: De Boer, Proc. Natl. Acad. Sci. USA, 80:21–25, 1983; $P_1$-system: Remaut, Gene, 15:81–93, 1981). It would be ideal if the external influences required for the formation of the antigens were only to be present where the live vaccine came into contact with the immune system but not in the course of the infection process so that the infection process necessary for the immune response is not disturbed. However, this is hardly realizable in practice not only because the infection process and the initiation of contact with the immune system are biologically linked but also because the conditions at the site of action of the live vaccine, i.e. in certain areas of the body of the person to be vaccinated, can be purposefully controlled with the available means neither with respect to location nor with respect to time.

SUMMARY OF THE INVENTION

It is therefore the object of the present invention to introduce a genetic element into the construction of hybrid live vaccines which, on the one hand, allows the production of sufficiently large quantities of additional antigen at the immunological site of action and, on the other hand, does not interfere with the course of infection by the hybrid live vaccine and thus the expected immunological protection. This object was achieved by making the formation of the additional antigens of the hybrid live vaccine dependent on random genetic events which occur relatively frequently. This principle implies the existence of two subpopulations/phases which originate from the live vaccine, namely of the hybrid live vaccine itself (subpopulation/phase A) which does not produce any additional antigen and therefore reproduces without its properties changing in relation to the original strain and is capable of a normal course of infection and a normal immune response, and a subpopulation/phase B which may have lost these properties but is constantly newly regenerated from subpopulation A and releases large quantities of additional antigen at the site of action (see FIG. 1). Subpopulation A therefore has the task of guaranteeing a perfect course of infection while subpopulation B serves to build up an effective immune response to the additionally formed antigens.

BRIEF DESCRIPTION OF THE DRAWINGS

FIG. 1. shows a schematic representation of the spontaneous formatiaon of two sub-populations/phases (A and B) of a cellular live vaccine.

FIG. 2. shows an example of a specific DNA deletion in accordance with model I of the invention taking into account the role of the control enzyme.

FIG. 3. shows an example of a specific DNA inversion in accordance with model II of the invention.

FIG. 4. shows an example of a genetic element according to the present invention for a bacterial live vaccine and the nature of its effect.

FIG. 5. shows an immunoblot (Western) analysis of the formation of CT-B antigen in hybrid *S. typhimurium* SL3235 cells. In the figure, 20 ng of purified CT-B antigen obtained from Sigma is shown as a reference in lane 1 and 2.5 c $10^7$ cells corresponding to bacterial lysates in lanes 2 to 6; lane 2, *S. typhirmurium* SL3235 cultured at 37° C.; lane 3, *S. typhirmurium* SL3235 (pTK1) cultured at 28° C.; lane 4, *S. typhirmurium* SL3235 (pTK1) cultured at 37° C.; lane 5, *S. typhirmurium* SL3235 (pYZ17) cultured at 28° C. Position "a" refers to an unspecific cross reaction in the blot, position "b" to the precursor of the CT-B antigen and position "c" to the mature CT-B antigen. The samples are obtained and the immunoblot is performed acording to Klauser (EMBO J., 9: 1991–1999, 1990).

DETAILED DESCRIPTION OF THE INVENTION

Random events which lead to the formation of subpopulations are natural and can mostly be traced back to changes in the DNA, so-called (programmed) DNA reorganisations (Borst, Science, 235:658–667, 1987). In principle, all naturally-observed mechanisms of DNA reorganisation can be used for the task set, provided that they can be reproduced suitably frequently in the hybrid live vaccine. The frequency of the formation of subpopulation B is preferably 0,1% to 50% per cell and cell generation; in particular cases, the frequency can, however, be higher or lower. Particularly suitable for application in a hybrid live vaccine are simple mechanisms of DNA reorganisation which occur at specific sites, such as inversion (Craig, Cell, 41:649–650, 1985) or deletion by resolution of transposon cointegration (Grindley, Annual Rev. Biochem., 54:863–896, 1985) of a DNA segment. However, other site-specific DNA reorganisations or such DNA reorganisations which are based on slipped-strand-mispairing (Levinson, Mol. Biol. Evol. 4:203–221, 1987; Stern, Cell, 47:61–71, 1986) seem suitable for the cited object.

It must be the purpose of the cited spontaneously occurring DNA reorganisation in a live vaccine to lead directly or indirectly to the production of additional antigen, i.e. to the formation of subpopulation B which produces the antigen. This occurs very simply e.g. by positioning an expression signal (for example the promoter) of a gene by DNA reorganisation in front of the gene such that said gene changes from a non-expressed to an expressed state. All variants of this principle are possible; but they all have the goal of bringing about a change in the expression of a gene by DNA reorganisation (see FIG. 2 and FIG. 3). It usually makes sense to switch on genes by DNA reorganisation although the opposite is also possible.

The gene switched on by DNA reorganisation can, on the one hand (model 1), be the gene coding for an additional antigen or (if the additional gene is not a protein but an enzymatic synthesis product, e.g. a carbohydrate) a gene required for the antigen synthesis, or, on the other hand (model II), a gene encoding a protein which controls the expression of the actual gene coding for the antigen. Model I is thus a system which by DNA reorganisation directly codes for the synthesis of the additional antigen or for an enzyme required for the synthesis while model II represents a system which allows the production of the additional antigen via a cascade system (see FIG. 2 and FIG. 3). The cascade system can be realized e.g. in that the gene directly controlled by DNA reorganisation codes for an RNA polymerase which is specific for the promoter preceding the gene coding for the antigen, or a gene regulator which in another specific manner induces the expression of the gene coding for the antigen (e.g. T7 polymerase: Studier, Meth. Enzymol. 185:60–89, 1990; lac system: De Boer, Proc. Natl. Acad. Sci. USA, 80:21–25, 1983). In this case too, there are all the possibilities of variation which nature offers. Whilst model I is on the one hand less complicated, the application of model II has advantages because high levels of expression can be achieved after one single DNA reorganisation due to the increasing effect of the cascade. Furthermore, with this model several genes which code for different additional antigens within one hybrid live vaccine can be switched on at the same time.

The realization of the described system is technically particularly simple in bacterial live vaccines. The genetic element capable of DNA reorganisation can be held in bacteria e.g. on a plasmid or introduced in the genome by means of a phage, a transposon or by homologous recombination. In the case of the cascade model II, the antigen-encoding genes, which have special sites for the binding of the gene products of the element capable of DNA reorganisation, can be introduced in a similar manner by using conventional techniques.

Depending on the principle of the underlying DNA reorganisation enzymes (referred to here as "control enzymes") are necessary which have to be provided by the cell so that DNA reorganisation can take place at all. In the case of an inversion according to the principle of the phage Mu an invertase is necessary, for example, besides cellular factors (Kahmann, Cell, 41:771–780, 1985); in the case of a deletion corresponding to the mechanism of the resolution of transposon cointegration the enzyme resolvase is necessary, for example, (Reed, Cell, 25:713–719, 1981); the formation of replicative circles corresponding to the replication of filamentous phages requires inter alia the gene 2 product of the phage (Meyer, Nature, 296:828–832, 1982). These enzymes as well as the DNA structure at which they attack (referred to here as "target sites"; e.g.: Mertens, EMBO J., 7:1219–1227, 1988), offer a suitable basis from which to regulate the frequency with which DNA reorganisation forms the additional antigen and thus to determine the ratio of populations A and B. Manipulation of the expression of the control enzymes or the target sites by genetic engineering makes it possible to adjust this ratio exactly to the desired ratio of the populations. However, it is also conceivable to subject the control enzymes in turn to a superordinate regulatory control in order to change the ratio of populations A and B by external influences (e.g. in dependence on the temperature) (see FIG. 2). Here, too, there are possibilities of variation as desired and given in the state of molecular biology.

The conventional methods of molecular biology serve for the construction of genetic elements which undergo DNA reorganisation. Moreover, it is advantageous to firstly clone such genetic elements in cells which do not synthesise control enzymes in order to keep them stable for manipulation and construction purposes. After preparation such elements can be inserted into the genome of the live vaccine by the conventional methods of molecular biology or can be kept extrachromosomally as a plasmid. The same applies to the genes which code for the control enzymes as well as with respect to genes indirectly or directly coding for antigens in the case of model II.

The final hybrid live vaccine is administered in a suitable manner (e.g. by oral dosage or by injection) to the individual to be protected. The administered dose of the hybrid live vaccine usually corresponds to that for the corresponding non-hybrid live vaccine.

EXAMPLES

Example 1

Construction of an invertable DNA element for the production of CT-B antigen (*Vibrio cholerae* toxin B—subunit) in Salmonella.

The genetic organisation of the invertable DNA element described here is represented in FIG. 4. The element is contained on the plasmid pYZ17 and was constructed by using the following genes or other nucleotide sequences:

The gin gene is derived from the plasmid pLMugin-X16 (Mertens, EMBO J. 3:2415–2421, 1984) and was removed from there firstly as partially cleaved PvuI fragment which still contained the PvuI cleavage site contained in the gin gene itself as the only uncleaved PvuI cleavage site. This PvuI fragment was provided with EcoRI linkers at its ends and after cleavage with EcoRI and BamHI isolated as a BamHI/EcoRI fragment. This fragment was linked at the BamHI cleavage site with a synthetic BamHI/ClaI fragment (5'-GGATAAACCGATACAATTAAAGGCTCCTTTTGGAGCCTTTTTTTTTGGAGATTTTCAACGTG-3') (SEQ. ID. NO.:1) of the terminator of bacteriophage fd so that a recombinant EcoRI/ClaI fragment was obtained.

The cI857-gene fragment was isolated from the plasmid pRK248 (Bernard, Gene 5:59–76, 1979) by partial cleavage with HindII and subsequent ligation with an XhoI linker as an XhoI/Cla fragment.

The EcoRI/ClaI gin fragment was ligated to the cI857 gene fragment via the ClaI cleavage site and incorporated as an EcoRI/XhoI fragment into a derivative (pYZ13) of the plasmid pBT192 (Zahm, Mol. Gen. Genet., 194:188–194, 1984) which carries an additional (EcoRI/ClaI/XhoI/BglII) polylinker region.

The $P_1$ promoter was isolated as an XhoII fragment from the plasmid pLC2833 (Remaut, Gene 22:103–113, 1983) and linked via the BclI cleavage site at both ends with two synthetic BclI/XhoI oligonucleotides (5'-GATCATTTACCGTTTCCTGTAAACCGAGGTTTTGGATAAC-3') (SEQ. ID. NO.:2) which correspond to the IR sequences (inverted repeats). The resulting fragment consisting of the sequence "IR-$P_1$-IR" was inserted into the singular XhoI cleavage of plasmid pfdA4 (Geider, Gene 33:341–349, 1985).

The rrnB T1 transcriptional terminator was obtained as a SalI/XhoI fragment with the nucleotide sequence XhoI 5'9—(SEQ. ID. NO.: 3).

The promoterless CT-B encoding ctxB gene fragment was isolated from plasmid pTK1 (Klauser, EMBO J. 8:1991–1999, 1990) after cleavage with ClaI and subsequent linkage with a BglII linker as a BglII/SalI fragment.

The plasmid pYZ17 was constructed from the above-mentioned components in the following manner:

The SalI/XhoI T1 terminator fragment was inserted into the singular XhoI cleavage of plasmid pYZ13 and tested for the orientation of the remaining intact XhoI cleavage. Derivatives from pYZ13 which carried the remaining XhoI cleavage site distally to the cI857 gene of pYZ13 were called pYZ15. The XhoI IR-$P_1$-IR fragment was inserted into the remaining XhoI cleavage site of pYZ16 so that the $P_1$ promoter was orientated to the cI857 gene. This plasmid (pYZ16) was identified by an asymmetric EcoRI cleavage (FIG. 4). Finally the $neo^r$ gene contained in pYZ16 was replaced by the ctxB fragment by cleavage with BglII/SalI and subsequent ligation to give pYZ17 (FIG. 4). Since pYZ17 possesses a further EcoRI cleavage site downstream from gin besides the EcoRI cleavage site within the invertable PI promoter fragment, the orientation of the promoter can be determined very easily by cleavage with EcoRI, and the inversion of the promoters can be followed up very easily. The fractionation of the EcoRI cleavage products in an agarose gel results in two bands of defined size of phase A of plasmid pYZ17 corresponding to about 4960 bp and 1840 bp or two bands of defined size of phase B of the same plasmid corresponding to 4630 bp and 2170 bp.

The construction and analysis of the described plasmids were carried out according to the methods described in Sambrook (Molecular Cloning, 2nd ed., 1989, Cold Spring Harbor Laboratory Press). For explanation of the function of the invertable elements on plasmid pYZ17 see the legend to FIG. 4.

Example 2

Oral immunisation of BALB/c mice against CT-B antigen using a two-phase *Salmonella typhimurium* live vaccine

*Salmonella typhimurium* SL3235 (Hoiseth, Nature 291:238–239, 1981) was transformed according to the $MgCl_2/CaCl_2$ method (Lederberg, J. Bacteriol., 119:1072–1074, 1974) in separate preparations by plasmids pYZ17 and pTK1. The transformants were frozen in LB medium containing 15% glycerin and kept at −75° C. Before the immunisation experiment these strains were firstly incubated overnight on LB plates containing ampicillin (100 mg/ml) at 28° C. Single colonies were then inoculated in 10 ml liquid LB medium containing ampicillin (50 mg/ml) and cultivated overnight at 28° C. 5 ml of these overnight cultures were then added to 20 ml LB medium having a temperature of 28° C. and containing ampicillin (50 mg/ml) and incubated for a further 4 hours at 28° C. The cultivated bacteria were subsequently harvested by centrifugation, washed in 10 ml saline (0.8% NaCl) and finally suspended in 2 ml saline.

The mice used for immunisation (BALB/c) were given water but no food for 16 hours before the vaccination. All the mice were each given an oral dose of 0.2 ml 50% saturated $Na_2HCO_3$ solution. The mice were then divided up into groups of 5 and 30 minutes later were each given 0.2 ml of the prepared bacteria suspension administered gastrally with a blunt vaccination cannula: S. typhimurium SL3235 (group 1), S. typhimurium SL3235/pTK1 (group 2) or S. typhimurium SL3235/pYZ17 (group 3). The oral immunisation took place at 3 intervals (day 0, 7 and 14) with the same dosage each time. On day 20, serum and intestinal fluid were collected (Manning, FEMS Microbiol. Lett., 28:317–321, 1985). Protease inhibitor was added to the removed intestinal fluid (Elson, J. Immunol. Meth., 67:101–108, 1984). The samples of the mice were pooled according to the groups and determined by means of class-specific goat-antimouse antibodies in the ELISA test with respect to their specific antibody titer (Elson, J. Immunol. Meth., 67:101–108, 1984). The results are shown in Table 1.

Discussion

The present invention is illustrated by the following figures in combination with the description and the examples.

In FIG. 2, X represents the antigen-encoding gene which is separated in phase A from its promoter ($P_X$) by a transcription terminating segment (U) and is therefore not expressed while in phase B the promoter is positioned directly in front of the gene X so that said gene is expressed. The deletion of the DNA segment U occurs by site-specific recombination at the sites IRS ("internal resolution sites" of the transposon Tn3) by the enzyme resolvase (TnpR of the transposon Tn3; here: closed, downwards pointing triangle). For this it is important that the two IRS sites whose nucleotide sequence is defined, are orientated in the same direction and are preferably localised within some 100 to 1000 base pairs on the same DNA molecule. The frequency of the deletion event can be determined by a number of factors, for example by slight sequence changes of one or both IRS sites or by the quantity of resolvase present in the cell. The quantity of this enzyme present in turn depends on the efficiency of the expression of the resolvase-encoding gene R. Provided that this gene in combination with its promoter ($P_R$) possesses an operator ($O_R$) on which transcription regulators can bind, it is possible in principle to regulate the frequency of the DNA reorganisation (deletion of segment U) via the expression levels of the control-enzyme-encoding gene (R) by external influences, e.g. temperature.

In FIG. 3, the genes X and Y represent antigen-encoding genes which are contained e.g. on a plasmid of a hybrid bacterial live vaccine in any arrangement. Promoters ($P_X$ and $P_Y$) proceed these genes and are specific for certain RNA polymerases (e.g. the polymerase of phage T7) which are not formed by the live vaccines/bacterial cells themselves. In phase A the genes X and Y cannot be expressed since the specific polymerase is lacking. However, the live vaccine/bacterial cell contains the gene (S) which codes for this polymerase. The gene S can now be activated e.g. by DNA inversion whereby the promoter Ps is positioned directly in front of the polymerase gene S by the inversion of a segment so that said gene is expressed. The inversion of the DNA segment containing the promoter is catalysed (e.g. in analogy to the G segment of the bacteriophage Mu) by an enzyme (gin/invertase) which attacks at well-defined target sites (IR/inverted repeats) which hold the opposite orientation on the DNA. The frequency with which the inversion of the fragment carrying the promoter occurs depends on several factors (inter alia the quantity of the invertase present in the cell and the structure of the IR sites at which it attacks) and can be individually adjusted or changed by manipulation by genetic engineering. In this example, the site-specific inversion of a DNA segment thus initiates a cascade which finally effects the activation of the antigen-encoding genes X and Y.

In FIG. 4, the sketches A and B are the two phases of an invertable element, corresponding to how this can be present in the subpopulations A or B after introduction into a bacterial strain. The element shown essentially corresponds to model I (direct expression of the antigen gene) and possesses a superordinate regulatory control function which is dependent on the temperature as an external influence. In phase A the promoter $P_1$ (PL) responsible for the expression of the antigen gene is directed in the direction of the c1857 gene, which codes for a superordinate temperature sensitive repressor, and the gin gene, which codes for the control enzyme. The consequence of this is that a repressor which is able to function is formed at the permissive temperature of 28° C. and reduces the transcription from the $P_1$ promoter (PL). At a higher temperature (e.g. 37° C.) the transcription of the $P_1$ promoter (PL) is increased since the repressor is inactivated at least partially under such external influences. The temperature-dependent increase in the transcription also causes a corresponding increase in the expression of the following gin gene which as a control enzyme catalyses the inversion of the promoter at the target sites. Thus, the frequency of the inversion is also increased by a higher temperature and thus the transition of the invertable element in phase B. However, the inversion at a lowered temperature is not completely prevented since the gin gene is always expressed on a low level anyway and, moreover, because the host cell itself which is used as the live vaccine usually possesses an active gene similar to gin.

Figure 4A:
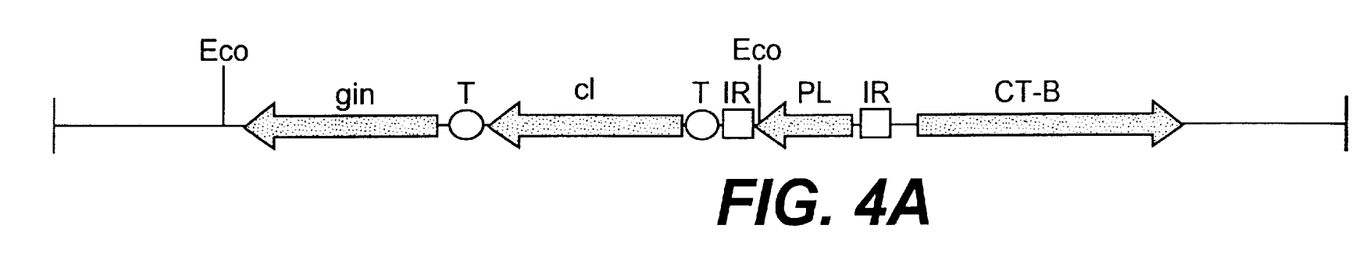
Figure 4B:
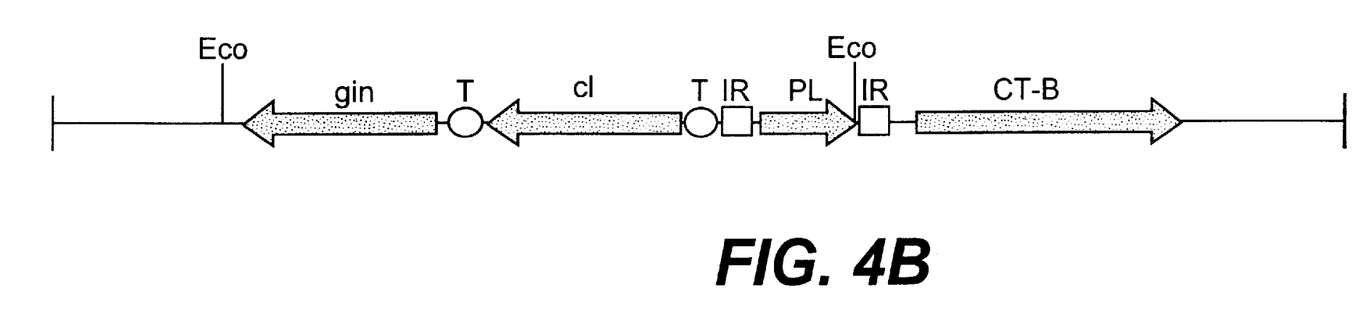

The inversion of the promoter causes less repressor and less control enzyme to be formed on the one hand and the antigen-encoding gene (CT-B) to be strongly expressed by means of the inverted promoter and due to the weaker formation of the cI repressor on the other hand.

In the above example, the invertable element is contained in the Salmonella typhimurium live vaccine (SL3235) on the plasmid pYZ17. Since this plasmid is present in several copies per bacterial cell, elements of both phase A and phase B can be present in a single bacterial cell. This results in additional interactions between the plasmids of phases A and B which cause a fractionation of the live vaccine not only in two subpopulations but also in the intermediates in between. If this is not desired, this can be easily taken care of by integration of the invertable element into the chromosome of the live vaccine or by cloning the element on a single copy plasmid.

Figure 5:
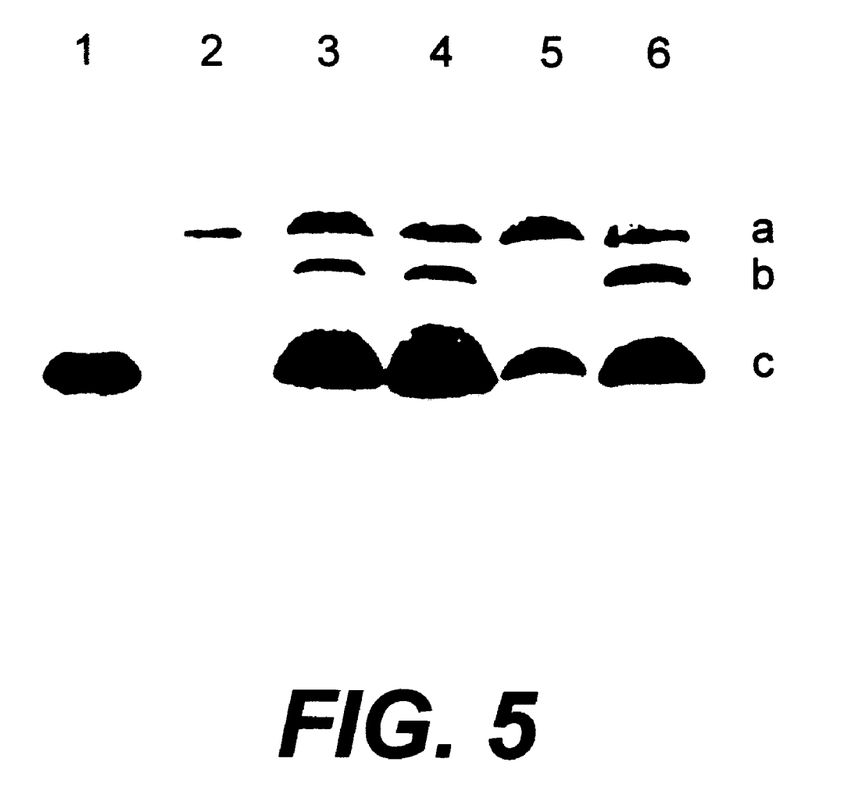

For further functional analysis of the invertable element contained in plasmid pYZ17 on the plasmid pYZ17 see also FIG. 5 and Tab. 1. In the drawing the abbreviations mean as follows: Eco, EcoRI restriction sites for the analysis of the phase state of the invertable element; gin (also gin in the text), the gene coding for the control enzyme (invertase); T, transcription terminators for the reduction of the gene expression; cI (more precisely referred to in the text as cI857), the gene coding for the temperature-sensitive regulator (repressor); IR, the target sites of the invertase (inverted repeats); PL (also referred to in the text as $P_1$), the invertable promoter which is regulatable by the cI857 repressor; CT-B, the gene (ctxB) coding for the antigen (*V. cholerae* toxin B-subunit).

Detailed Description of the Invention

FIG. 5 shows evidence of the formation of CT-B antigen by the invertible element of plasmid pYZ17 in *S. typhimurium* SL3235 in comparison with plasmid pTK1 (Klauser, EMBO J., 9:1991–1999, 1990).

It is apparent that *S. typhimurium* SL3235 (pYZ17) produces very little CT-B antigen at 28° C. in contrast to at 37° C. It is further evident that in contrast thereto the formation of CT-B antigen in the reference strain S. typhimurium SL3235 (pTK1) is independent of temperature and that in this strain in relation to S. typhimurium SL3235 (pYZ17), which was cultured at 37° C., less CT-B precursor protein is accumulated. The latter reflects the formation of little CT-B antigen in subpopulation A and much CT-B antigen in subpopulation B in S. typhimurium SL3235 (pYZ17) cultured at 37° C.: The formation of much CT-B in only a few cells leads to a hold-up in the conversion from precursor into mature CT-B antigen.

Tab. 1 Humoral immune response after oral immunisation of BALB/c mice with hybrid *Salmonella typhimurium* SL3235 strains.

The results of the experiment described in Example 2 are represented. The antibody titers stated therein correspond to those dilution levels of the samples which only just give a positive result in the ELISA test.

TABLE I

| | ELISA titer | | |
|---|---|---|---|
| | Serum | | Intestinal lavage |
| | IgG | IgA | IgG |
| SL3235 | 20 | 8 | 8 |
| SL3235 (pTK1) | 640 | 16 | 16 |
| SL3235 (pYZ17) | 10240 | 128 | 64 |

What is claimed is:

1. An immunogenic composition comprising a living cell or a virus expressing a first immunogenic antigen and further comprising recombinant DNA encoding at least one second, immunogenic antigen heterologous to said cell or virus, wherein said at least one second antigen is expressed under the control of a DNA reorganization occurring in said cell or in a cell infected with said virus, the DNA reorganization resulting in a phase variation in the cell or virus, wherein the DNA reorganization occurs in a subject to which said living cell or virus is administered.

2. An immunogenic composition comprising a population A of a living cell or virus, said population A being infectious to a subject and expressing a first antigen and being immunogenic as to said first antigen, said living cell or virus further comprising at least one recombinant DNA comprising:

i) at least one polynucleotide sequence encoding at least one second antigen heterologous to said cell or virus;

ii) a promoter; and iii) at least one DNA element executing a DNA reorganization;

wherein said living cell or virus or said at least one recombinant DNA further comprises:

iv) a polynucleotide that encodes an enzyme that effects said DNA reorganization via said at least one DNA element iii);

and wherein said population A forms a subpopulation A' by DNA reorganization of said recombinant DNA, whereby subpopulation A' expresses said first and at least one second antigens and is immunogenic as to said first and at least one second antigens.

3. The immunogenic composition of claim 2, wherein said promoter ii) is operatively linked to said polynucleotide i) and to said at least one DNA element iii).

4. The immunogenic composition of claim 3, wherein said promoter ii) is one from which transcription is effected by a specific polymerase or that is regulated by a specific gene regulator.

5. The immunogenic composition of claim 2, wherein said at least one recombinant DNA further comprises:

v) a regulatory polynucleotide encoding a specific polymerase or a specific gene regulator; and vi) a second promoter from which transcription is effected by said specific polymerase or that is regulated by said specific gene regulator.

6. The immunogenic composition of claim 5, wherein said regulatory polynucleotide v) is operatively linked to said promoter ii) and is operatively linked to at least one DNA element iii), whereby said specific polymerase or specific gene regulator v) is expressed upon said DNA reorganization, and said polynucleotide encoding said at least one second antigen i) is operatively linked to said promoter vi) from which transcription is effected by said specific polymerase or that is regulated by said specific gene regulator.

7. The immunogenic composition of claim 5, wherein said at least one recombinant DNA further comprises:

vii) a second regulatory polynucleotide encoding a second specific polymerase or a second specific gene regulator, wherein transcription from said promoter ii) is effected by said second specific polymerase or is regulated by said second specific gene regulator.

8. The immunogenic composition according to claim 1 or 2, wherein said DNA reorganization is a specific DNA inversion.

9. The immunogenic composition according to claim 1 or 2, wherein said DNA reorganization is a specific deletion.

10. The immunogenic composition according to claim 1 or 2, wherein said DNA reorganization is a specific DNA replication process.

11. The immunogenic composition according to claim 1 or 2, wherein said DNA reorganization occurs due to slipped-strand-mispairing.

12. The immunogenic composition according to claim 2, wherein said DNA reorganization is effected by an enzyme that is expressed under the control of a regulatable promoter.

13. The immunogenic composition according to claim 1 or 2, wherein said at least one recombinant DNA is present in a chromosome of said cell.

14. The immunogenic composition according to claim 1 or 2, wherein said at least one recombinant DNA is present on a plasmid.

15. The immunogenic composition according to claim 1 or 2, wherein said recombinant DNA is present in at least two copies.

16. The immunogenic composition according to claim 1 or 2, that comprises a bacterium or a eukaryotic cell.

17. The immunogenic composition according to claim 1 or 2, wherein said DNA reorganization resulting in expression of said at least one second antigen occurs at a frequency ranging from 0.1% to 50% per cell or virus per generation.

18. The immunogenic composition according to claim 1 or 2, that comprises a cell of *Salmonella typhimurium* and wherein said at least one second antigen is the CTX-B protein of *Vibrio cholerae*.

19. An immunogenic composition comprising a population A of a living cell or virus, said population A being infectious to a subject and expressing a first antigen, said living cell or virus further comprising at least one recombinant DNA comprising:

i) a polynucleotide that encodes an enzyme that catalyzes a DNA inversion;

ii) at least one polynucleotide sequence encoding at least one second antigen heterologous to said cell or virus;

iii) a polynucleotide that encodes a specific gene regulator or a specific polymerase;

iv) DNA elements for executing a DNA inversion catalyzed by said enzyme, said DNA protein binding elements being located between said polynucleotides ii) and iii); and v) a promoter located between said DNA elements so that said promoter is operatively linked to either the polynucleotide ii) or the polynucleotide iii) upon said DNA inversion, wherein said promoter is regulated by said specific gene regulator or transcribed by said specific polymerase;

wherein said population A forms a subpopulation A' by said DNA inversion, whereby subpopulation A' expresses said first and at least one second antigens and is immunogenic as to said first and at least one second antigens.

20. An immunogenic composition comprising a population A of a living cell or virus, said population A being infectious to a subject and expressing a first antigen, said living cell or virus further comprising at least one recombinant DNA comprising:

i) DNA elements executing a DNA reorganization;

ii) a promoter;

iii) at least one polynucleotide sequence encoding at least one second antigen heterologous to said cell or virus, located between said DNA elements so that said promoter ii) is linked to or unlinked from said at least one polynucleotide sequence encoding at least one second antigen upon said DNA reorganization; and iv) a polynucleotide that encodes an enzyme that effects said DNA reorganization via said DNA elements i);

and wherein said population A forms a subpopulation A' by DNA reorganization of said recombinant DNA, whereby subpopulation A' expresses said first and at least one second antigens and is immunogenic as to said first and at least one second antigens.

21. An immunogenic composition comprising a population A of said living cell or virus, said population A being infectious to a subject and expressing a first antigen, said living cell or virus further comprising a recombinant DNA comprising:

i) DNA elements executing a DNA reorganization;

ii) a first promoter;

iii) a regulatory polynucleotide encoding a specific polymerase or a specific gene regulator, located between said DNA protein binding elements so that said promoter ii) is linked to or unlinked from said regulatory polynucleotide encoding a specific polymerase or a specific gene regulator upon said DNA reorganization;

iv) a second promoter from which transcription is effected by said specific polymerase or that is regulated by said specific gene regulator operatively linked to at least one polynucleotide sequence encoding at least one second antigen heterologous to said cell or virus; and v) a polynucleotide that encodes an enzyme that effects said DNA reorganization via said DNA elements i);

wherein said population A forms a subpopulation A' by DNA reorganization of said recombinant DNA, whereby subpopulation A' expresses said first and at least one second antigens and is immunogenic as to said first and at least one second antigens.

22. An immunogenic composition comprising a population A of a living cell or virus, said population A being infectious to a subject and expressing a first antigen, said living cell or virus further comprising at least one recombinant DNA comprising:

i) DNA elements executing a DNA reorganization;

ii) a promoter;

iii) at least one polynucleotide sequence encoding at least one second antigen heterologous to said cell or virus, wherein said promoter ii) is linked to or unlinked from said at least one polynucleotide sequence encoding at least one second antigen upon said DNA reorganization; and wherein said living cell or virus or said at least one recombinant DNA further comprises:

iv) a polynucleotide that encodes an enzyme that effects said DNA reorganization via said DNA elements i);

and wherein said population A forms a subpopulation A' by DNA reorganization of said recombinant DNA, whereby subpopulation A' expresses said first and at least one second antigens and is immunogenic as to said first and at least one second antigens.

23. An immunogenic composition comprising a population A of said living cell or virus, said population A being infectious to a subject and expressing a first antigen, said living cell or virus further comprising a recombinant DNA comprising:

i) DNA elements executing a DNA reorganization;

ii) a regulatory polynucleotide encoding a specific polymerase or a specific gene regulator;

iii) a first promoter located between said DNA protein binding elements so that said first promoter is linked to or unlinked from said regulatory polynucleotide ii) encoding a specific polymerase or a specific gene regulator upon said DNA reorganization;

iv) a second promoter from which transcription is effected by said specific polymerase or that is regulated by said specific gene regulator operatively linked to at least one polynucleotide sequence encoding at least a second antigen heterologous to said cell or virus; and v) a polynucleotide that encodes an enzyme that effects said DNA reorganization via said DNA elements i);

wherein said population A forms a subpopulation A' by DNA reorganization of said recombinant DNA, whereby subpopulation A' expresses said first and at least one second antigens and is immunogenic as to said first and at least one second antigens.

24. The immunogenic composition according to any one of the claims 2–6, wherein said population A forms said subpopulation A' upon administration of said immunogenic composition to a subject.

25. A method for immunizing a subject comprising administering the immunogenic composition of claim 1 or 2 to said subject in an amount effective to raise an immune response to said at least one second antigen.

* * * * *